(12) United States Patent
Martin et al.

(10) Patent No.: US 7,838,700 B2
(45) Date of Patent: Nov. 23, 2010

(54) RECOVERY AND RECYCLING OF CHIRAL TARTARIC ACID RESOLVING AGENTS

(75) Inventors: Steve Martin, Cramlington (GB); Daniele Piergentili, Mannheim (IT)

(73) Assignee: Aesica Pharmaceuticals, Cramlington (GB)

( * ) Notice: Subject to any disclaimer, the term of this patent is extended or adjusted under 35 U.S.C. 154(b) by 550 days.

(21) Appl. No.: 10/495,359

(22) PCT Filed: Nov. 8, 2002

(86) PCT No.: PCT/EP02/12494

§ 371 (c)(1), (2), (4) Date: Nov. 23, 2004

(87) PCT Pub. No.: WO03/042132

PCT Pub. Date: May 22, 2003

(65) Prior Publication Data

US 2005/0085665 A1    Apr. 21, 2005

(30) Foreign Application Priority Data

Nov. 14, 2001   (GB) .................................. 0127346.5

(51) Int. Cl.
*C07B 57/00*   (2006.01)
*C07C 51/00*   (2006.01)

(52) U.S. Cl. ........................................ 562/401; 562/515

(58) Field of Classification Search ................. 562/515, 562/401; 252/364
See application file for complete search history.

(56) References Cited

FOREIGN PATENT DOCUMENTS

| CN | 1273966 | * | 11/2000 |
|---|---|---|---|
| JP | 09-176115 | * | 8/1997 |
| WO | 98/01424 | | 1/1998 |
| WO | 01/46148 | | 6/2001 |

OTHER PUBLICATIONS

Database, Chemical Abstract No. 127:121629CA and JP 09 176115.

* cited by examiner

*Primary Examiner*—Taylor Victor Oh
(74) *Attorney, Agent, or Firm*—Novak Druce + Quigg LLP

(57) ABSTRACT

A process for the recovery of substituted tartaric acid resolving agents from resolution process liquors comprising organic solvents, wherein the substituted tartaric acid derivatives are neutralised by adding a base, extracted into an aqueous phase and crystallized from the aqueous phase by addition of a mineral acid in the presence of an organic solvent.

9 Claims, No Drawings

RECOVERY AND RECYCLING OF CHIRAL TARTARIC ACID RESOLVING AGENTS

This invention relates to a novel process for the recovery of chiral substituted tartaric acid resolving agents from process liquors in a form of sufficient purity to enable their recycle in the corresponding resolution process.

Chemical processes for the synthesis of optically active amine compounds frequently use optically active organic acid resolving agents to allow the required enantiomer to be preferentially crystallised as a salt with the resolving agent. The required optically active amine can then be regenerated by basification of the salt.

Particular examples of such resolution processes are found in the synthesis of N-benzylpiperidines and tetrahydropyridine derivatives which are useful intermediates in the synthesis of (−)-trans-4-(4-fluorophenyl)-3-(3,4-methylenedioxyphenoxymethyl) piperidine and its salts, a drug having antidepressive effects.

One such process is disclosed in patent WO 98/01424, which describes the resolution of a racemic tertiary amine intermediate to form the optically pure salt of the required absolute configuration with a substituted tartaric acid resolving agent. The optically active amine is regenerated by reaction of the salt with a suitable base to give the substituted tartaric acid as a salt in aqueous solution as a byproduct.

In WO 01/46148 a process for the manufacture of (−)trans piperidine carbinols is disclosed wherein the racemic piperidine carbinol is contacted with (−)ditoluol tartaric acid, followed by isolation of the crystalline salt and regeneration of the ditoluoltartaric acid by addition of an aqueous inorganic base.

According to the Japanese laid open application No. 09176115 optically active tartaric acid derivatives can be recovered from a resolving process for optically active aminopyrrolidones by treatment of the salts with alkalis in water, followed by extraction of the aqueous layer with organic solvents and addition of mineral acids to the aqueous layer.

Examples of resolving agents used in such resolution processes include (+)-di-O,O'-toluoyl-(D)-tartaric acid, (−)-di-O,O'-toluoyl-(L)-tartaric acid, (+)-di-O,O'-benzoyl-(D)-tartaric acid, (−)-di-O,O'-benzoyl-(L)-tartaric acid. Examples of such structures are shown in FIG. 1.

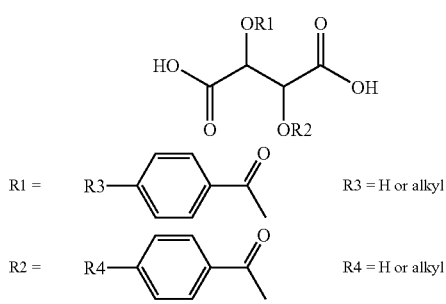

Figure 1

Such resolving agents are typically expensive to manufacture or purchase.

Previous to this invention, methods used to recover substituted tartaric acid resolving agents have been found to give poor yields and low purity due to the prevalence of unwanted esterification, transesterification, or de-esterification reactions. The poor efficiency of previously used recovery processes are also the result of the need to extract the substituted tartaric acid into a water-immiscible organic solvent, then to crystallise it from a different solvent with consequent extended time for distillation. Such solvent exchange operations increase the losses due to the unwanted side reactions referred to above.

It is an object of the present invention to provide an improved process for the recovery of substituted tartaric acid resolving agents from resolution mother liquors comprising organic solvents.

We have found that this object is achieved by a process wherein the substituted tartaric acid derivatives are neutralised by adding a base, extracted into an aqueous phase and crystallised from the aqueous phase by addition of a mineral acid in the presence of a water soluble organic co-solvent.

This invention relates to an efficient method for recovery of the substituted tartaric acid resolving agent from the resolution mother liquor or from the aqueous phase from regeneration of the chiral salt in a form which may be recycled for use in further resolution reactions. Accordingly, the term "mother liquor" as used herein means the process liquor from the resolution process as well as the process liquor of the regeneration process.

Typically such process liquors comprise one or more organic solvents in addition to the resolving agent and the optically active amine. Typical organic solvents used for the resolving process are ketones, e.g. acetone, alcohols such as for instance methanol, aromatic hydrocarbons, e.g. toluene, ethers such as for instance tetrahydrofurane or mixtures thereof. Preferably the organic solvent is only poorly miscible with water or water immiscible, if not a water miscible solvent needs to be distilled of and replaced by a poorly water miscible or immiscible solvent, e.g. toluene.

In this invention the mother liquor may be reacted, optionally after solvent exchange, with a suitable base to give a salt of the substituted tartaric acid resolving agent which is dissolved in water to allow separation from organic by-products which may be dissolved in a water immiscible organic solvent. The aqueous phase obtained contains the substituted tartaric acid resolving agent as its salt with the base and is similar in composition to the solution obtained from the regeneration of the optically active amine from its salt with the resolving agent.

The base used for neutralisation of the amine salt of the substituted tartaric acid resolving agent may be a hydroxide, carbonate or hydrogen carbonate salt of an alkali or alkaline earth metal or optionally substituted ammonia. Preferably the base is sodium or potassium carbonate or hydrogen carbonate or ammonia. More preferably the base is sodium hydrogen carbonate. The base is preferably added in the form of an aqueous solution. The concentration of the base in the solution depends on the type of base used.

The co-solvent added to the aqueous solution containing the substituted tartaric acid resolving agent may be any water soluble or partly watersoluble organic solvent, preferably a $C_{1\ to\ 10}$-alcohol, more preferably 2-butanol.

The mineral acid may be any strong acid, preferably sulphuric, phosphoric, hydrochloric, hydrobromic or nitric acid, more preferably hydrochloric acid. The mineral acid is added in amounts sufficient to recover tartaric acid derivative in the form of the free acid.

The recovery of the tartaric acid derivatives is typically carried out at 20 to 50° C. The product is filtered off and dried, typically under reduced pressure.

The process according to the present invention is particularly advantageous in the recovery of tartaric acid resolving agents from mother liquors in the manufacture of optically pure (+)-1-benzyl-3-hydroxymethyl-4-(-4-fluorophenyl)-1,2,3,6-tetrahydropyridine.

Unexpectedly it has been discovered that addition of a suitable organic solvent together with a mineral acid results in crystallisation of the substituted tartaric acid resolving agent directly from the aqueous mixture, without the need for phase separation or solvent exchanges, and in a manner which is reproducible on a commercial scale.

A particularly advantageous feature of the present invention is the isolation of substituted tartaric acid resolving agent in a crystalline form of suitable purity for reuse in a resolution reaction without additional purification. The substituted tartaric acid resolving agent is typically crystallised as a solvate with the co-solvent used, of a purity in excess of 95% excluding the residual solvent. The optical purity of the substituted tartaric acid resolving agent is not significantly affected by the recovery process.

The present invention includes use of such a solvate of the substituted tartaric acid resolving agent in a resolution reaction.

EXAMPLES

Example 1

A solution (16.1 liters) containing (+)-di-O,O'-toluoyl-(D)-tartaric acid (about 1106 g) and 1-benzyl-3-hydroxymethyl-4-(4-fluorophenyl)-1,2,3,6-tetrahydropyridine dissolved in methanol was concentrated by distillation of methanol and diluted with toluene (5.0 kg). The mixture was warmed to 40° C. and 1 M sodium hydrogen carbonate solution (6.3 liters) was added slowly. The mixture was stirred for 30 minutes then the lower aqueous phase containing (+)-di-O,O'-toluoyl-(D)-tartaric acid as its disodium salt was separated off. The organic phase was stirred with water (1.8 liters) at 40° C. for 30 minutes. The lower aqueous phase was separated off. The aqueous phases were combined and 2-butanol (2.5 liters) was added. The mixture was warmed to 40° C. and hydrochloric acid (552 ml) was added slowly. The mixture was cooled to 10° C. and stirred for 30 minutes then the solid (+)-di-O,O'-toluoyl-(D)-tartaric acid was collected by filtration and washed twice with water (2×2.2 liters). The damp solid was dried at 50° C. under reduced pressure. (+)-Di-O,O'-toluoyl-(D)-tartaric acid (1270 g) was obtained as its 2-butanol solvate, HPLC assay 72%/28% retained solvent, 83% of theory.

Example 2

(+)-1-benzyl-3-hydroxymethyl-4-(4-fluorophenyl)-1,2,3,6-tetrahydropyridine (+)-di-O,O'-p-toluoyl-D-tartrate (1.8 kg) was suspended in toluene (6.9 liters). The mixture was warmed to 35° C. and 1 M sodium hydrogen carbonate solution (6.6 liters) was added slowly. The mixture was stirred at 35 to 40° C. for 2 hours then the lower aqueous phase containing (+)-di-O,O'-toluoyl-(D)-tartaric acid as its disodium salt was separated off. The organic phase was stirred with water (4.4 liters) at 35 to 40° C. for 30 minutes. The lower aqueous phase was separated off. The aqueous phases were combined and 2-butanol (2.9 liters) was added. The mixture was warmed to 40° C. and hydrochloric acid (720 ml) was added slowly. The mixture was cooled to 10° C. and stirred for 30 minutes then the solid (+)-di-0,0'-toluoyl-(D)-tartaric acid was collected by filtration and washed twice with water (2×1.8 liters). The damp solid was dried at 50° C. under reduced pressure (10-300 mbar). (+)-Di-O,O'-toluoyl-(D)-tartaric acid (1310 g) was obtained as its 2-butanol solvate, HPLC assay 76%/24% retained solvent, 98% of theory.

The invention claimed is:

1. A process for recovering a substituted tartaric acid resolving agent from a resolution process liquor,
wherein the resolution process liquor comprises an organic solvent, and a substituted tartaric acid resolving agent of the formula:

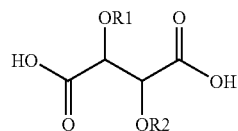

where

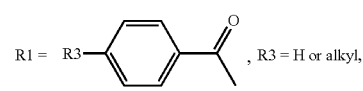, R3 = H or alkyl,

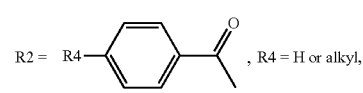, R4 = H or alkyl, said process comprising:
A) adding a base to the resolution process liquor to neutralize the substituted tartaric acid resolving agent;
B) extracting the liquor obtained in A) into an aqueous phase; and
C) adding a mineral acid and a water soluble or partly water soluble organic co-solvent to the aqueous phase obtained in B) to crystallize a substituted tartaric acid resolving agent from the aqueous phase.

2. A process according to claim 1 wherein the substituted tartaric acid resolving agent is chosen from (+)-di-O,O'-toluoyl-(D)-tartaric acid, (−)-di-O,O'-toluoyl-(L)-tartaric acid, (+)-di-O,O'-benzoyl-(D)-tartaric acid, or (−)-di-O,O'-benzoyl-(L)-tartaric acid.

3. A process according to claim 1 wherein the base is added as an aqueous solution.

4. A process according to claim 1 wherein the substituted tartaric acid resolving agent is neutralized by a hydroxide, carbonate or hydrogen carbonate salt of an alkali or alkaline earth metal or ammonia.

5. A process according to claim 1 wherein the organic co-solvent is a $C_{1\ to\ 10}$-alcohol.

6. A process according to claim 1 wherein the organic co-solvent is 2-butanol.

7. A process according to claim 1 wherein the mineral acid is hydrochloric acid, hydrobromic acid, or sulfuric acid.

8. A process according to claim 1 wherein the mineral acid is hydrochloric acid.

9. A process according to claim 1 wherein the substituted tartaric acid resolving agent is crystallised in the form of a solvate with the co-solvent.

* * * * *